United States Patent
Bai et al.

(10) Patent No.: US 12,102,736 B2
(45) Date of Patent: Oct. 1, 2024

(54) POLYURETHANE BASED MEDICAL ARTICLES

(71) Applicant: Becton, Dickinson and Company, Franklin Lakes, NJ (US)

(72) Inventors: He Bai, Sandy, UT (US); Marc W. Weimer, South Jordan, UT (US); James Freasier, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 61 days.

(21) Appl. No.: 17/680,646

(22) Filed: Feb. 25, 2022

(65) Prior Publication Data
US 2022/0265904 A1 Aug. 25, 2022

Related U.S. Application Data

(60) Provisional application No. 63/153,810, filed on Feb. 25, 2021.

(51) Int. Cl.
*A61L 29/06* (2006.01)
*A61L 29/16* (2006.01)
(Continued)

(52) U.S. Cl.
CPC ............... *A61L 29/06* (2013.01); *A61L 29/16* (2013.01); *C08G 18/3206* (2013.01);
(Continued)

(58) Field of Classification Search
CPC ...... A61L 29/06; A61L 29/16; A61L 2420/00; C08G 18/3206; C08G 18/7671; C08G 2150/00
See application file for complete search history.

(56) References Cited

U.S. PATENT DOCUMENTS 3,071,856 A 1/1963 Fischbein
3,361,700 A 1/1968 Archer et al.
(Continued)

FOREIGN PATENT DOCUMENTS

AU 2010224421 B9 12/2010
AU 2015206417 B2 7/2015
(Continued)

OTHER PUBLICATIONS

PCT International Search Report and Written Opinion in PCT/US2022/017870 dated May 25, 2022, 14 pages.
(Continued)

*Primary Examiner* — Blessing M Fubara
(74) *Attorney, Agent, or Firm* — Servilla Whitney LLC

(57) ABSTRACT

Medical articles formed from a polyurethane-based resin including an ionically-charged modifier provide enhanced properties. The polyurethane-based resin is a reaction product of ingredients comprising: a diisocyanate; a diol chain extender; a polyglycol; and an ionically-charged modifier incorporated into a backbone, as a side chain, or both of the polyurethane-based resin. Embodiments include the ionically-charged modifier is a combination of anionic and cationic modifiers. Embodiments include the ionically-charged modifier is zwitterionic. Medical articles herein either have inherent antimicrobial and/or anti-fouling characteristics or can easily bond ionic active agents to provide desirable material properties, including antimicrobial, anti-fouling, and/or radiopacity.

18 Claims, 1 Drawing Sheet

(51) Int. Cl.
*C08G 18/32* (2006.01)
*C08G 18/76* (2006.01)

(52) U.S. Cl.
CPC ...... *C08G 18/7671* (2013.01); *A61L 2420/00* (2013.01); *C08G 2150/00* (2013.01)

(56) References Cited

U.S. PATENT DOCUMENTS

| | | |
|---|---|---|
| 3,441,142 A | 4/1969 | Oja |
| 3,562,352 A | 2/1971 | Nyilas |
| 3,574,673 A | 4/1971 | Schweiger |
| 3,616,935 A | 11/1971 | Love et al. |
| 3,617,344 A | 11/1971 | Leininger et al. |
| 3,634,123 A | 1/1972 | Eriksson et al. |
| 3,645,955 A | 2/1972 | Flynn |
| 3,755,218 A | 8/1973 | Yen et al. |
| 3,759,788 A | 9/1973 | Gajewski et al. |
| 3,810,781 A | 5/1974 | Eriksson et al. |
| 3,846,353 A | 11/1974 | Grotta |
| 4,057,595 A | 11/1977 | Rauner et al. |
| 4,100,309 A | 7/1978 | Micklus et al. |
| 4,182,787 A | 1/1980 | Goossens et al. |
| 4,182,828 A | 1/1980 | Reischl et al. |
| 4,188,426 A | 2/1980 | Auerbach |
| 4,250,072 A | 2/1981 | Flynn |
| 4,283,447 A | 8/1981 | Flynn |
| 4,326,532 A | 4/1982 | Hammar |
| 4,349,467 A | 9/1982 | Williams et al. |
| 4,373,009 A | 2/1983 | Winn |
| 4,454,309 A | 6/1984 | Gould et al. |
| 4,521,564 A | 6/1985 | Solomon et al. |
| 4,579,879 A | 4/1986 | Flynn |
| 4,581,390 A | 4/1986 | Flynn |
| 4,589,873 A | 5/1986 | Schwartz et al. |
| 4,613,517 A | 9/1986 | Williams et al. |
| 4,642,242 A | 2/1987 | Solomon et al. |
| 4,642,267 A | 2/1987 | Creasy et al. |
| 4,647,643 A | 3/1987 | Zdrahala et al. |
| 4,657,024 A | 4/1987 | Coneys |
| 4,664,657 A | 5/1987 | Williamitis et al. |
| 4,668,221 A | 5/1987 | Luther |
| 4,678,660 A | 7/1987 | McGary et al. |
| 4,713,402 A | 12/1987 | Solomon |
| 4,720,521 A | 1/1988 | Spielvogel et al. |
| 4,722,344 A | 2/1988 | Cambron et al. |
| 4,767,414 A | 8/1988 | Williams et al. |
| 4,841,007 A | 6/1989 | Zdrahala et al. |
| 4,842,889 A | 6/1989 | Hu et al. |
| 4,844,986 A | 7/1989 | Karakelle et al. |
| 4,865,870 A | 9/1989 | Hu et al. |
| 4,880,883 A | 11/1989 | Grasel et al. |
| 4,883,699 A | 11/1989 | Aniuk et al. |
| 4,925,668 A | 5/1990 | Khan et al. |
| 4,935,480 A | 6/1990 | Zdrahala et al. |
| 4,939,007 A | 7/1990 | Hu et al. |
| 4,990,537 A | 2/1991 | Okuyama et al. |
| 4,994,047 A | 2/1991 | Walker et al. |
| 5,004,456 A | 4/1991 | Botterbusch et al. |
| 5,013,306 A | 5/1991 | Solomon et al. |
| 5,032,666 A | 7/1991 | Hu et al. |
| 5,059,269 A | 10/1991 | Hu et al. |
| 5,061,254 A | 10/1991 | Karakelle et al. |
| 5,084,315 A | 1/1992 | Karimi et al. |
| 5,102,401 A | 4/1992 | Lambert et al. |
| 5,159,050 A | 10/1992 | Onwumere |
| 5,159,051 A | 10/1992 | Onwumere et al. |
| 5,226,899 A | 7/1993 | Lee et al. |
| 5,250,649 A | 10/1993 | Onwumere et al. |
| 5,266,669 A | 11/1993 | Onwunaka et al. |
| 5,281,677 A | 1/1994 | Onwunaka et al. |
| 5,302,385 A | 4/1994 | Khan et al. |
| 5,322,659 A | 6/1994 | Walder et al. |
| 5,453,099 A | 9/1995 | Lee et al. |
| 5,545,708 A * | 8/1996 | Onwunaka ......... C08G 18/6674 264/165 |
| 6,261,271 B1 | 7/2001 | Solomon et al. |
| 7,459,167 B1 | 12/2008 | Sengupta et al. |
| 8,691,887 B2 | 4/2014 | Ou-Yang |
| 8,754,020 B2 | 6/2014 | Ou-Yang |
| 8,821,455 B2 | 9/2014 | Burkholz et al. |
| 9,345,806 B2 | 5/2016 | Tonelli et al. |
| 2003/0018156 A1 | 1/2003 | Meijs et al. |
| 2006/0263329 A1 | 11/2006 | Eemeta et al. |
| 2007/0248566 A1 | 10/2007 | Chen et al. |
| 2012/0208916 A1 | 8/2012 | Cavitt et al. |
| 2013/0158518 A1 | 6/2013 | Li et al. |
| 2015/0306345 A1* | 10/2015 | Burkholz ............... A61M 39/20 604/265 |
| 2016/0024419 A1 | 1/2016 | Hermel-Davidock et al. |
| 2017/0049109 A1 | 2/2017 | Wynne et al. |
| 2017/0107320 A1 | 4/2017 | Zhou et al. |
| 2017/0174911 A1 | 6/2017 | Nowak et al. |
| 2018/0146665 A1 | 5/2018 | Liu et al. |
| 2018/0237721 A1 | 8/2018 | Hermel-Davidock et al. |
| 2019/0106525 A1 | 4/2019 | Becker et al. |
| 2020/0093969 A1 | 3/2020 | Bai et al. |
| 2020/0095515 A1 | 3/2020 | Bai et al. |

FOREIGN PATENT DOCUMENTS

| | | |
|---|---|---|
| CA | 2716502 C | 11/2010 |
| CA | 2937132 A1 | 7/2015 |
| CN | 101880371 A | 11/2010 |
| CN | 102046008 A | 5/2011 |
| CN | 102316965 A | 1/2012 |
| CN | 102585149 A | 7/2012 |
| CN | 103242505 A | 8/2013 |
| CN | 103333312 A | 10/2013 |
| CN | 103665291 A | 3/2014 |
| CN | 104403086 A | 3/2015 |
| CN | 105273594 A | 1/2016 |
| CN | 107614587 A | 1/2018 |
| CN | 109438670 A | 3/2019 |
| CN | 111777738 A | 10/2020 |
| DE | 10050495 A1 | 4/2002 |
| DE | 102016225500 A1 | 6/2018 |
| EP | 0184465 A2 | 6/1986 |
| EP | 0359273 A2 | 3/1990 |
| EP | 0452123 A1 | 10/1991 |
| EP | 0548745 B1 | 3/2002 |
| GB | 2332438 A | 6/1999 |
| JP | 2007031368 A | 2/2007 |
| WO | 2012027729 A1 | 3/2012 |
| WO | 2016172460 A1 | 10/2016 |
| WO | 2017014597 A1 | 1/2017 |
| WO | 2017015072 A1 | 1/2017 |
| WO | 2017015073 A1 | 1/2017 |
| WO | 2017172740 A1 | 10/2017 |
| WO | 2018011748 A1 | 1/2018 |
| WO | 2018029133 A1 | 2/2018 |
| WO | 2018140911 A1 | 8/2018 |
| WO | 2019101771 A1 | 5/2019 |
| WO | WO-2019204712 A1 * | 10/2019 ............ A61L 27/18 |
| WO | 2020021203 A1 | 1/2020 |
| WO | 2020030670 A1 | 2/2020 |
| WO | 2020068617 A1 | 4/2020 |
| WO | 2020068619 A1 | 4/2020 |

OTHER PUBLICATIONS

PCT International Search Report and Written Opinion in PCT/US2022/017872 dated May 25, 2022, 11 pages.
PCT International Search Report and Written Opinion in PCT/US2019/052351 dated Dec. 10, 2019, 14 pages.
PCT International Search Report and Written Opinion in PCT/US2019/052355 dated Dec. 12, 2019, 14 pages.
"Solvay Specialty Polymers, "FLUOROLINK® for Low Surface Energy Coatings," 2013".
Arkles, Barry, et al., "Positive Tactile Interaction Coatings", Paint & Coatings Industry magazine, Issued Jul. 2017, vol. 23, No. 7, pp. 1-8.

(56) References Cited

OTHER PUBLICATIONS

Tonelli, Claudio, et al., "New Perfluoropolyether Soft Segment Containing Polyurethanes", Journal of Applied Polymer Science. Vol. 57, 1031-1042 (1995).

Vaidya, Ashish, et al., "Synthesis and Surface Properties of Environmentally Responsive Segmented Polyurethanes", Journal of Colloid and Interface Science, vol. 249, No. 1, May 1, 2002, pp. 235-245.

Phunphoem, Sivaphol, "Synthesis of Cationic Waterborne Polyurethanes from Waste Frying Oil as Antibacterial Film Coatings", International Journal of Polymer Science, vol. 2019, Article ID 2903158, Oct. 9, 2019.

Wang, Xuechuan, et al., "Study on the Structure Activity Relationship of Amphoteric Ionic Waterborne Polyurethane", Functional Materials, Issue 4, Apr. 30, 2016.

Wang, Chun-Hua, et al., "Synthesis, characterization and antibacterial properties of polyurethane material functionalized with quaternary ammonium salt", Polymer Journal (2016) 48, 259-265, Nov. 18, 2015.

Search Report and in Chinese Application No. 202210172352X dated Jul. 24, 2023, 4 pages.

Search Report and in Chinese Application No. 2022101724560 dated Jul. 24, 2023, 3 pages.

\* cited by examiner

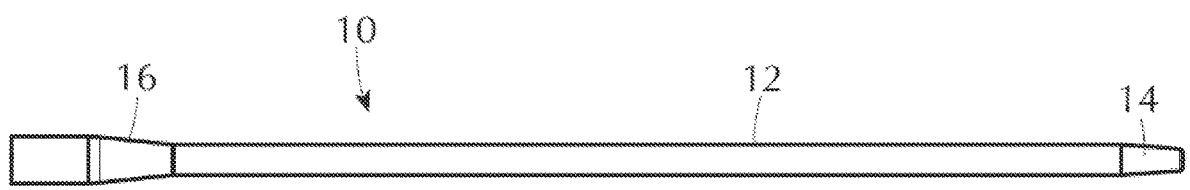

POLYURETHANE BASED MEDICAL ARTICLES

CROSS-REFERENCE TO RELATED APPLICATIONS

This application claims priority to U.S. Provisional Application No. 63/153,810, filed Feb. 25, 2021, the entire disclosure of which is hereby incorporated by reference herein.

TECHNICAL FIELD

The present disclosure relates to a polyurethane-based resin including a backbone of a diisocyanate, a polyglycol, and a diol chain extender, which also includes addition of at least one ionically-charged modifier into the backbone, as a side chain or both. Embodiments include the ionically-charged modifier is a combination of anionic and cationic modifiers. Embodiments include the ionically-charged modifier is zwitterionic. Medical articles made therefrom either have inherent antimicrobial and/or anti-fouling characteristics or can easily bond ionic active agents to provide desirable material properties, including antimicrobial, anti-fouling, and/or radiopacity.

BACKGROUND

Infusion therapy medical devices, such as syringe cannulas and catheters used for sampling or medicament administration, typically have components that are in direct contact of bodily fluid that can cause infection. For example, catheter-related bloodstream infections may be caused by colonization of microorganisms, which can occur in patients whose treatment includes intravascular catheters and I.V. access devices. These infections can lead to illness and excess medical costs. Impregnating and/or coating catheters with various antimicrobial agents (e.g., chlorhexidine, silver or other antibiotics) is a common approach that has been implemented to prevent these infections.

Some blood contact devices have the potential to generate thrombus. When blood contacts a foreign material, a complex series of events occur. These involve protein deposition, cellular adhesion and aggregation, and activation of blood coagulation schemes. Thrombogenicity has conventionally been counteracted by the use of anticoagulants such as heparin. Attachment of heparin to otherwise thrombogenic polymeric surfaces may be achieved with various surface coating techniques.

Impregnating catheters directly with antimicrobial/antithrombogenic agents does not create chemical bonding between active agents and polymer substrates, thus devices would lose antifouling efficacy in a short time and it would also create regulatory concerns, e.g., heparin-induced thrombocytopenia (HIT). Surface coating techniques are to heparinize the polymer substrate or bond an antibiotic to the polymer substrate by chemical bonding to achieve non-leaching or controlled release of active agents. However, these coating techniques would require priming of polymer substrates (e.g., chemical or plasma treatments), followed by multiple steps of surface coating, which would complicate the medical device manufacturing process and significantly increase manufacturing costs.

Thus, there is a need for polymeric resins, in particular polyurethane resins, that either has inherent antimicrobial and/or anti-fouling characteristics or can easily bond antimicrobial/antithrombogenic agents to achieve antimicrobial and/or anti-fouling characteristics.

SUMMARY

One or more embodiments are directed to a medical article formed from a polyurethane-based resin, which is a reaction product of ingredients comprising: a diisocyanate; a diol chain extender; a polyglycol; and an ionic modifier (a combination of anionic and cationic modifiers or a zwitterionic modifier) incorporated into a backbone, as a side chain, or both of the polyurethane-based resin formed by the diisocyanate, the polyglycol, and the diol chain extender; the polyurethane-based resin having a hard segment content in a range of from 25% to 75% by weight and a soft segment content of the resin is in a range of from 75% to 25% by weight.

An additional embodiment is directed to a medical article formed from a polyurethane-based resin, which is a reaction product of ingredients consisting essentially of: 4,4'-diphenylmethane diisocyanate (MDI) as the diisocyanate; 1,4-butanediol as the diol chain extender; a polytetramethylene ether glycol as the polyglycol; 2,2-bis(hydroxymethyl)butyric acid (BHMBA) and/or bis-1,4-((2-hydroxypropoxy)-2-propoxy)-butane sulfonate sodium salt (SULFADIOL®-7Q) as the anionic modifier; and bis(2-hydroxyethyl) dimethylammonium chloride (BHDAC) as the cationic modifier.

Additional embodiments are directed methods of infusion therapy comprising: infusing a material from a medical article according to any embodiment herein into a patient.

BRIEF DESCRIPTION OF THE DRAWINGS

FIG. 1 is a plan view of an exemplary medical device.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

The following terms shall have, for the purposes of this application, the respective meanings set forth below.

Polyglycols include but are not limited to: polyalkylene glycol, polyester glycol, and polycarbonate glycol. A non-limiting specific example of polyalkylene glycol is polyether glycol. A polyether glycol is a moderate molecular weight oligomer derived from an alkylene oxide, containing both ether linkages and glycol termination.

A chain extender is a short chain (low molecular weight) branched or unbranched diol, diamine or amino alcohol of up to 10 carbon atoms or mixtures thereof. Such hydroxyl- and/or amine-terminated compounds are used during polymerization to impart desired properties to a polymer.

An ionically-charged modifier is a compound exhibiting a charge that enhances a basic polyurethane structure of a diisocyanate; a diol chain extender; and a polyglycol. The ionically-charged modifier herein comprises a combination of anionic and cationic modifiers or a zwitterionic modifier that make the polyurethane zwitterionic in nature to render the resulting medical article with desirable properties. The desired properties include passive reduction of bacterial biofilm colony formation and antifouling property. The anionic functional moieties include but not limited to —$SO_3^-$ and/or —$COO^-$. The cationic functional moieties include but not limited to quaternary ammonium. The anionic and cationic functional moieties can be incorporated into a backbone, as a side chain, or both. The anionic and cationic functional moieties can be delivered as a polyglycol or as a diol chain extender, or as a diisocyanate.

Antimicrobial agents that can be used for bonding with anionic functional moieties of the zwitterionic polyurethane include any cationic antibiotics, e.g., chlorhexidine acetate, chlorhexidine gluconate, silver sulfadiazine, benzalkonium chloride, cetylpyridinium chloride, etc. In addition, cationic quaternary ammonium and guanidine containing biocides, cationic antimicrobial polymers, antimicrobial peptides or peptide-mimics as well as antifouling phospholipids or phospholipid-mimics can also be ionically bonded with anionic functional moieties of the zwitterionic polyurethane to actively and/or passively provide advantages of enhanced surface properties including antimicrobial and/or anti-fouling. Furthermore, cationic radiopaque agent, e.g., barium and bismuth cations, can also be ionically bonded with anionic functional moieties of the zwitterionic polyurethane to provide medical article desirable radiopacity.

Antimicrobial agents that can be used for bonding with cationic functional moieties of the zwitterionic polyurethane include any anionic antibiotics, e.g., cloxacillin salt, cefoxitin salt, cefazolin salt, penicillin salt, or derivatives thereof. Similarly, anionic antithrombogenic agents, e.g., heparin salt, can be ionically bonded with cationic functional moieties of the zwitterionic polyurethane to provide medical article desirable antithrombogenic properties.

In addition, the skilled artisan will recognize that other cationic and/or anionic biocides and anticoagulants of either small molecules or macromolecules can also be used for bonding with ionic functional groups of the zwitterionic polyurethane.

A low-surface energy modifying oligomer (moderate molecular weight), as described in WO 2020/068617 A1 and WO 2020/068619 A1, which is optional in embodiments herein, is a compound that enhances a basic polyurethane structure of a diisocyanate; a diol chain extender; a polyglycol; and an ionic modifier. Modifying oligomers, which are different from polyglycols and ionic modifiers, contain functional moieties (e.g., fluoroether and/or silicone) that migrate onto the polyurethane surface to render the resulting medical article with additional desirable surface properties including self-lubricating and antifouling property. Modifying oligomers may have at least one, preferably two, or more than two, alcohol moieties (C—OH). The alcohol moieties may be located along a backbone of the oligomer. The alcohol moieties may be located at an end of the oligomer. In a detailed embodiment, the oligomer terminates with an alcohol moiety.

Isocyanate index is defined as the molar ratio of the total isocyanate groups in the diisocyanate to the total hydroxyl and/or amino groups presented in polyols and extenders. In general, the polyurethane becomes harder with an increasing isocyanate index. There is, however, a point beyond which the hardness does not increase and the other physical properties begin to deteriorate.

As used herein, the term "consists essentially of" means that the material does not contain any other components in amounts that may alter the properties of the polyurethane material.

Principles and embodiments of the present disclosure relate generally to thermoplastic polyurethane (TPU) materials having improved properties, and methods of preparing and using them. Provided are medical articles, for example, catheter tubing, that either have inherent antimicrobial and/or anti-fouling characteristics or can easily bond ionic active agents to provide desirable material properties, including antimicrobial, anti-fouling, and/or radiopacity. Included with traditional polyurethane monomers is an ionically-charged modifier. Herein, the ionically-charged modifier is a combination of anionic and cationic modifiers or a zwitterionic modifier, whose functional moieties (e.g., —$SO_3^-$ and/or —$COO^-$ and quaternary ammonium) can be introduced into soft segments of the TPU materials using polyglycols and/or optional low-surface energy modifying oligomers with ionic functionalities or hard segments of TPU materials using diol chain extenders and/or diisocyanates with ionic functionalities.

In FIG. 1, an exemplary medical article in the form of a catheter is illustrated. Tubing made from polyurethane resins as disclosed herein forms the catheter, which is shaped as needed to receive other components for forming vascular access devices. Catheter 10 comprises a primary conduit 12, which is tubing in its as-extruded form. At a distal end, a tip 14 is formed by a tipping process. At a proximal end, a flange 16 is formed as needed for receipt of other components including but not limited to catheter adapters. Exemplary vascular access devices may include a needle further to the catheter for access to blood vessels.

The articles comprise a polyurethane-based resin that is a reaction product of the following ingredients: a diisocyanate; a diol chain extender; a polyglycol; and an ionic modifier (a combination of anionic and cationic modifiers or a zwitterionic modifier) incorporated into a backbone of the polyurethane-based resin, as a side chain or both. Incorporation into backbone means that ionic functionalities (e.g., —$SO_3^-$ and/or —$COO^-$ and quaternary ammonium) are directly linked to the polyurethane backbone chain; incorporation as a side chain means that there is at least one carbon chain spacer between ionic functionalities and the polyurethane backbone chain. The polyurethane-based resin comprises a hard segment content in a range of from 25% to 75% by weight and a soft segment content of the resin in a range of from 75% to 25% by weight.

In one or more embodiments, the anionic modifier is incorporated into the polyurethane-based resin in an amount of greater than or equal to: 0.01 wt. %, 0.1 wt. %, 0.5 wt. %, 1 wt. %, 1.5 wt. %, 2 wt. %, 3 wt. %, 4 wt. % and 4.5 wt. % of the overall composition of the polyurethane-based resin. In one or more embodiments, the anionic modifier is incorporated into the polyurethane-based resin in an amount of less than or equal to: 75 wt. %, 50 wt. %, 25 wt. %, 10 wt. %, 9.5 wt. %, 9.0 wt. %, 8.5 wt. %, 8.0 wt. %, 7.5 wt. %, 7.0 wt. %, 6.5 wt. % or 6.0 wt. % of the overall composition of the polyurethane-based resin. In one or more embodiments, the anionic modifier is incorporated into the polyurethane-based resin in an amount ranging from greater than or equal to 0.01 to less than or equal to 75 wt. %, and all values and subranges therebetween, including greater than or equal to 0.5 to less than or equal to 50 wt. %, greater than or equal to 1 to less than or equal to 25 wt. %, and all values and subranges there between; including: greater than or equal to: 0.01 wt. %, 0.1 wt. %, 0.5 wt. %, 1 wt. %, 1.5 wt. %, 2 wt. %, 3 wt. %, 4 wt. % and 4.5 wt. % to less than or equal to: 75 wt. %, 50 wt. %, 25 wt. %, 10 wt. %, 9.5 wt. %, 9.0 wt. %, 8.5 wt. %, 8.0 wt. %, 7.5 wt. %, 7.0 wt. %, 6.5 wt. %, 6.0 wt. % of the overall composition of the polyurethane-based resin.

In one or more embodiments, the cationic modifier is incorporated into the polyurethane-based resin in an amount of greater than or equal to: 0.01 wt. %, 0.1 wt. %, 0.5 wt. %, 1 wt. %, 1.5 wt. %, 2 wt. %, 3 wt. %, 4 wt. % and 4.5 wt. % of the overall composition of the polyurethane-based resin. In one or more embodiments, the cationic modifier is incorporated into the polyurethane-based resin in an amount of less than or equal to: 10 wt. %, 9.5 wt. %, 9.0 wt. %, 8.5 wt. %, 8.0 wt. %, 7.5 wt. %, 7.0 wt. %, 6.5 wt. % or 6.0 wt. % of the overall composition of the polyurethane-based resin. In one or more embodiments, the cationic modifier is incorporated into the polyurethane-based resin in an amount ranging from greater than or equal to 0.01 to less than or equal to 10 wt. %, and all values and subranges therebetween, including greater than or equal to 0.5 to less than or equal to 7.5 wt. %, greater than or equal to 1.0 to less than or equal to 6.0 wt. %, and all values and subranges there between; including: greater than or equal to: 0.01 wt. %, 0.1 wt. %, 0.5 wt. %, 1 wt. %, 1.5 wt. %, 2 wt. %, 3 wt. %, 4 wt. % and 4.5 wt. % to less than or equal to: 10 wt. %, 9.5 wt. %, 9.0 wt. %, 8.5 wt. %, 8.0 wt. %, 7.5 wt. %, 7.0 wt. %, 6.5 wt. %, 6.0 wt. % of the overall composition of the polyurethane-based resin.

In one or more embodiments, the zwitterionic modifier is incorporated into the polyurethane-based resin in an amount of greater than or equal to: 0.01 wt. %, 0.1 wt. %, 0.5 wt. %, 1 wt. %, 1.5 wt. %, 2 wt. %, 3 wt. %, 4 wt. % and 4.5 wt. % of the overall composition of the polyurethane-based resin. In one or more embodiments, the zwitterionic modifier is incorporated into the polyurethane-based resin in an amount of less than or equal to: 10 wt. %, 9.5 wt. %, 9.0 wt. %, 8.5 wt. %, 8.0 wt. %, 7.5 wt. %, 7.0 wt. %, 6.5 wt. % or 6.0 wt. % of the overall composition of the polyurethane-based resin. In one or more embodiments, the zwitterionic modifier is incorporated into the polyurethane-based resin in an amount ranging from greater than or equal to 0.01 to less than or equal to 10 wt. %, and all values and subranges therebetween, including greater than or equal to 0.5 to less than or equal to 7.5 wt. %, greater than or equal to 1.0 to less than or equal to 6.0 wt. %, and all values and subranges there between; including: greater than or equal to: 0.01 wt. %, 0.1 wt. %, 0.5 wt. %, 1 wt. %, 1.5 wt. %, 2 wt. %, 3 wt. %, 4 wt. % and 4.5 wt. % to less than or equal to: 10 wt. %, 9.5 wt. %, 9.0 wt. %, 8.5 wt. %, 8.0 wt. %, 7.5 wt. %, 7.0 wt. %, 6.5 wt. %, 6.0 wt. % of the overall composition of the polyurethane-based resin.

The anionic modifier may comprise one or more of —$SO_3^-$ and/or $COO^-$ functional moieties. Non-limiting examples of the anionic modifiers are: bis-1,4-((2-hydroxypropoxy)-2-propoxy)-butane sulfonate sodium salt (SULFADIOL®-7Q); 2,3-dihydroxypropane-1-sulfonate sodium salt; N,N-bis(2-hydroxyethyl)-2-aminoethanesulfonate sodium salt; 2,2-bis(hydroxymethyl)propionic acid; 2,2-bis(hydroxymethyl)butyric acid (BHMBA); or combination thereof.

The cationic modifier may comprise one or more quaternary ammonium functional moieties. A non-limiting example of the cationic modifier with quaternary ammonium functional moiety is bis(2-hydroxyethyl)dimethylammonium chloride (BHDAC).

The zwitterionic modifier may comprise both anionic and cationic functional moieties. Non-limiting examples of the zwitterionic modifier with both anionic and cationic functional moieties are: N,N-bis(2-hydroxyethyl)-2-amino-ethanesulfonic acid; N,N-bis(2-hydroxyethyl)glycine; or combination thereof.

The polyurethane-based resin may be a reaction product of a diisocyanate; a diol chain extender; a polyglycol; and a combination of anionic and cationic modifiers. In an embodiment, the polyurethane-based resin is a reaction product of: a diisocyanate; a diol chain extender; a polyglycol; a bis-1,4-((2-hydroxypropoxy)-2-propoxy)-butane sulfonate sodium salt (SULFADIOL®-7Q) as the anionic modifier; and a bis(2-hydroxyethyl)dimethylammonium chloride (BHDAC) as the cationic modifier. In an embodiment, the polyurethane-based resin is a reaction product of: a diisocyanate; a diol chain extender; a polyglycol; a 2,3-dihydroxypropane-1-sulfonate sodium salt as the anionic modifier; and a bis(2-hydroxyethyl)dimethylammonium chloride (BHDAC) as the cationic modifier. In an embodiment, the polyurethane-based resin is a reaction product of: a diisocyanate; a diol chain extender; a polyglycol; a N,N-bis(2-hydroxyethyl)-2-aminoethanesulfonate sodium salt as the anionic modifier; and a bis(2-hydroxyethyl)dimethylammonium chloride (BHDAC) as the cationic modifier. In an embodiment, the polyurethane-based resin is a reaction product of: a diisocyanate; a diol chain extender; a polyglycol; a 2,2-bis(hydroxymethyl)propionic acid as the anionic modifier; and a bis(2-hydroxyethyl)dimethylammonium chloride (BHDAC) as the cationic modifier. In an embodiment, the polyurethane-based resin is a reaction product of: a diisocyanate; a diol chain extender; a polyglycol; a 2,2-bis(hydroxymethyl)butyric acid (BHMBA) as the anionic modifier; and a bis(2-hydroxyethyl)dimethylammonium chloride (BHDAC) as the cationic modifier. In an embodiment, the polyurethane-based resin is a reaction product of: a diisocyanate; a diol chain extender; a polyglycol; one or multiple anionic modifiers; and one or multiple cationic modifiers.

In a detailed embodiment, the polyurethane-based resin is a reaction product of ingredients consisting essentially of: 4,4'-diphenylmethane diisocyanate (MDI) as the diisocyanate; 1,4-butanediol as the diol chain extender; polytetramethylene ether glycol(s) as the polyglycols; 2,2-bis(hydroxymethyl)butyric acid (BHMBA) and/or bis-1,4-((2-hydroxypropoxy)-2-propoxy)-butane sulfonate sodium salt (SULFADIOL®-7Q) as the anionic modifier; and bis(2-hydroxyethyl)dimethylammonium chloride (BHDAC) as the cationic modifier.

The polyurethane-based resin may be a reaction product of a diisocyanate; a diol chain extender; a polyglycol; and a zwitterionic modifier (containing both anionic and cationic functional moieties). In an embodiment, the polyurethane-based resin is a reaction product of: a diisocyanate; a diol chain extender; a polyglycol; and a N,N-bis(2-hydroxyethyl)-2-amino-ethanesulfonic acid as the zwitterionic modifier. In an embodiment, the polyurethane-based resin is a reaction product of: a diisocyanate; a diol chain extender; a polyglycol; and a N,N-bis(2-hydroxyethyl)glycine as the zwitterionic modifier.

In a detailed embodiment, the polyurethane-based resin is a reaction product of ingredients consisting essentially of: 4,4'-diphenylmethane diisocyanate (MDI) as the diisocyanate; 1,4-butanediol as the diol chain extender; polytetramethylene ether glycol(s) as the polyglycols; and N,N-bis(2-hydroxyethyl)-2-amino-ethanesulfonic acid and/or N,N-bis(2-hydroxyethyl)glycine as the zwitterionic modifier.

In a detailed embodiment, the polyurethane-based resin is a reaction product of: a diisocyanate; a diol chain extender; a polyglycol; an ionic modifier (a combination of anionic and cationic modifiers or a zwitterionic modifier) incorporated into a backbone, as a side chain, or both of the polyurethane-based resin; and a low-surface energy modifying oligomer (as described in WO 2020/068617 A1 and WO 2020/068619 A1) incorporated into a backbone, as a side chain, or both of the polyurethane-based resin.

The zwitterionic polyurethane herein can be directly synthesized using an ionic modifier (a combination of anionic and cationic modifiers or a zwitterionic modifier) by a conventional one-step or two-step copolymerization process. Catalyst or solvent may be required. The synthesis can also be achieved by a variety of other synthesis techniques with or without catalyst/solvent understood by those skilled in the art. The zwitterionic polyurethane herein can also be formulated from a blend of two or more different polyurethane compositions, e.g., blending/compounding of existing anionic polyurethanes and cationic polyurethanes. Blending/compounding approach can allow for quick creation and characterization of new polyurethane compositions using the already existing polyurethane copolymers. Even though the micro-domain structure and molecular weight distribution may be different using direct copolymerization approach compared to blending/compounding approach, it is expected that comparable material properties will result based on a comparable overall polyurethane composition. Through structural and compositional design, the resulting zwitterionic polyurethane resins can potentially possess inherent antimicrobial and/or anti-fouling surface properties for medical device applications.

Antimicrobial agents that can be used for bonding with anionic functional moieties of the zwitterionic polyurethane include any cationic antibiotics. Non-limiting examples of the cationic antibiotics include chlorhexidine acetate, chlorhexidine gluconate, silver sulfadiazine, benzalkonium chloride and cetylpyridinium chloride. In addition, cationic quaternary ammonium and guanidine containing biocides, cationic antimicrobial polymers, antimicrobial peptides or peptide-mimics as well as antifouling phospholipids or phospholipid-mimics can also be ionically bonded with anionic functional moieties of the zwitterionic polyurethane to actively and/or passively provide advantages of enhanced surface properties including antimicrobial and/or anti-fouling. Furthermore, cationic radiopaque agent can also be ionically bonded with anionic functional moieties of the zwitterionic polyurethane to provide medical article desirable radiopacity. Non-limiting examples of the cationic radiopaque agent include barium and bismuth cations. Antimicrobial agents that can be used for bonding with cationic functional moieties of the zwitterionic polyurethane include any anionic antibiotics. Non-limiting examples of the anionic antibiotics include cloxacillin salt, cefoxitin salt, cefazolin salt, penicillin salt, or derivatives thereof. Non-limiting examples of the anionic antithrombogenic agents include heparin salt, or derivatives thereof. In addition, the skilled artisan will recognize that other cationic and/or anionic biocides and anticoagulants of either small molecules or macromolecules can also be used for bonding with ionic functional groups of the zwitterionic polyurethane. Ionic bonding of active agents can be achieved by solution imbibing technique or bulk mixing (e.g., thermal compounding or solvent mixing) technique. As a result, ionic antimicrobial, ionic antithrombogenic, and/or ionic radiopaque agents would be ionically bonded not only on zwitterionic TPU surface but also in the bulk zwitterionic TPU to render the resulting medical device desirable properties, including antimicrobial, anti-fouling, and/or radiopacity.

Polyurethanes

Polyurethane materials disclosed herein have enhanced surface properties, which may be tailored to fit different practical needs. Medical devices formed of these polyurethane materials are used to create a fluid channel from a medication reservoir to a patient in need thereof, where the fluid channel may be inserted into and in fluid communication with vascular vessels, or subcutaneous tissue, where the invasive medical device comprises any of the polyurethane materials as described herein.

Thermoplastic polyurethanes (TPUs) suitable for medical devices are typically synthesized from three basic components, a diisocyanate, a polyglycol, and a chain extender, usually a low molecular weight diol, diamine, amino alcohol or water. If the chain extender is a diol, the polyurethane consists entirely of urethane linkages. If the extender is water, amino alcohol or diamine, both urethane and urea linkages are present, which results in a polyurethaneurea (PUU). Inclusion of an amine-terminated polyether to the polyurethane synthesis also results in a polyurethaneurea. Device applications for thermoplastic polyurethanes include central venous catheters (CVCs), peripherally inserted central catheter (PICCs), and peripheral intravenous catheters (PIVCs).

Polyurethane and polyurea chemistries are based on the reactions of isocyanates with other hydrogen-containing compounds, where isocyanates are compounds having one or more isocyanate group ($-N=C=O$). Isocyanate compounds can be reacted with water ($H_2O$), alcohols ($R-OH$), amines ($R_x-NH_{(3-x)}$), ureas ($R-NH-CONH_2$), and amides ($R-CONH_2$). Certain polyurethanes may be thermoplastic elastomers (TPE), whereas other compositions may be highly cross-linked.

Thermoplastic polyurethanes comprise two-phases or microdomains conventionally termed hard segments and soft segments, and as a result are often referred to as segmented polyurethanes. The hard segments, which are generally of high crystallinity, form by localization of the portions of the polymer molecules which include the diisocyanate and chain extender(s). The soft segments, which are generally either non-crystalline or of low crystallinity, form from the polyglycol or the optional amine-terminated polyether. The hard segment content is determined by the weight percent of diisocyanate and chain extender in the polyurethane composition, and the soft segment content is the weight percent of polyglycol or polydiamine. The thermoplastic polyurethanes may be partly crystalline and/or partly elastomeric depending on the ratio of hard to soft segments. One of the factors which determine the properties of the polymer is the ratio of hard and soft segments. In general, the hard segment contributes to hardness, tensile strength, impact resistance, stiffness and modulus while the soft segment contributes to water absorption, elongation, elasticity and softness.

Polyurethane materials may be used as raw materials for catheter tubing via compounding, extrusion/coextrusion or molding.

The polyurethanes may be produced by the reaction of: a diisocyanate, a diol chain extender, at least one polyglycol, at least one ionically-charged modifier (a combination of anionic and cationic modifiers or a zwitterionic modifier), and optionally, a low-surface energy modifying oligomer. The polyurethane may have a hard segment content between 25% and 75% by weight, where a hard segment is the portion(s) of the polymer molecules which include the diisocyanate and the extender components, which are generally highly crystalline due to dipole-dipole interactions and/or hydrogen bonding. In contrast, the soft segments formed from the polyglycol portions and optionally the low-surface energy modifying oligomers between the diisocyanate of the polymer chains and generally are either amorphous or only partially crystalline due to the characteristics of the polyglycol(s) and modifying oligomer(s). In an embodiment, the hard segment content may be in the range of from 25% to 75% and the soft segment content may be in the range of from 75% to 25%. Herein, the ionically-charged modifier is a combination of anionic and cationic modifiers or a zwitterionic modifier, whose anionic and cationic functional moieties can be introduced into soft segments of the TPU materials using polyglycols and/or optional low-surface energy modifying oligomers with ionic functionalities or hard segments of TPU materials using diol chain extenders and/or diisocyanates with ionic functionalities. Non-limiting examples of the anionic functional moieties of the zwitterionic polyurethane include carboxylate —COO$^-$, sulfonate —SO$_3^-$ or combination thereof. In an embodiment, anionic moieties are introduced into hard segment of the TPU material using diol chain extender with anionic functionalities, e.g., 2,2-bis(hydroxymethyl)butyric acid (BHMBA). In another embodiment, anionic moieties are introduced into soft segment of the TPU material using polyglycol with anionic functionalities, e.g., bis-1,4-((2-hydroxypropoxy)-2-propoxy)-butane sulfonate sodium salt (SULFADIOL®-7Q). Non-limiting examples of the cationic functional moieties of the zwitterionic polyurethane include quaternary ammonium. In an embodiment, cationic moieties are introduced into hard segment of the TPU material using diol chain extender with cationic functionalities, e.g., bis(2-hydroxyethyl)dimethylammonium chloride (BHDAC).

Polymerization of the polyurethane may be a one-step or two-step copolymerization process. The process may require a catalyst, solvent, other additives, or a combination thereof. The synthesis may also be achieved by a variety of other synthesis techniques with or without catalyst/solvent understood by those skilled in the art. The zwitterionic polyurethane may also be formulated from a blend of two or more different polyurethane compositions, e.g., blending/compounding of existing anionic polyurethanes and cationic polyurethanes.

The diisocyanate may be selected from the group consisting of: an aliphatic diisocyanate, alicyclic diisocyanate and an aromatic diisocyanate. In various embodiments, the diisocyanate may be selected from the group consisting of: 4,4'-diphenylmethane diisocyanate (MDI), toluene diisocyanate (TDI), isophorone diisocyanate (IPDI), methylene-bis(4-cyclohexylisocyanate) (HMDI), or combinations thereof.

The diol chain extender may be selected from the group consisting of: ethylene glycol, 1,3-propylene glycol, 1,4-butanediol, neopentyl glycol, and alicyclic glycols having up to 10 carbon atoms.

The polyglycol may be selected from the group consisting of: polyalkylene glycol, polyester glycol, polycarbonate glycol, and combinations thereof. In an embodiment, the polyglycol comprises the polyalkylene glycol. In an embodiment, the polyalkylene glycol comprises a polytetramethylene ether glycol.

The polytetramethylene ether glycol may be of any desired molecular weight. The desired molecular weight is the molecular weight in the range of from 200 Da to 4000 Da, or 250 Da to 2900 Da. The polytetramethylene ether glycol (PTMEG) may be PTMEG250, PTMEG650, PTMEG1000, PTMEG1400, PTMEG1800, PTMEG2000, and PTMEG2900. PTMEG has the formula: HO(CH$_2$CH$_2$CH$_2$CH$_2$—O—)$_n$H, which may have an average value of n in the range of 3 to 40. A blend of two or more PTMEG250, PTMEG650, PTMEG1000, PTMEG1400, PTMEG1800, PTMEG2000, and PTMEG2900 may be used such. Reference to PTMEG250 means a polytetramethylene ether glycol having an average molecular weight in a range of 230 to 270 Da. Reference to PTMEG650 means a polytetramethylene ether glycol having an average molecular weight in a range of 625 to 675 Da. Reference to PTMEG1000 means a polytetramethylene ether glycol having an average molecular weight in a range of 950 to 1050 Da. Reference to PTMEG1400 means a polytetramethylene ether glycol having an average molecular weight in a range of 1350 to 1450 Da. Reference to PTMEG1800 means a polytetramethylene ether glycol having an average molecular weight in a range of 1700 to 1900 Da. Reference to PTMEG2000 means a polytetramethylene ether glycol having an average molecular weight in a range of 1900 to 2100 Da. Reference to PTMEG2900 means a polytetramethylene ether glycol having an average molecular weight in a range of 2825 to 2976 Da. In an embodiment, a preferred an average molecular weight of the combination is less than 1000 Da. In an embodiment, the polyol is a blend of two or more PTMEG having the formula: HO(CH$_2$CH$_2$CH$_2$CH$_2$—O—)$_n$H, where n has an average value in the range of 3 to 40. In one or more embodiments, the polyols is a blend of two or more PTMEG having the formula: HO(CH$_2$CH$_2$CH$_2$CH$_2$—O—)$_n$H, where n has an average value in the range of 3 to 40 and an average molecular weight of the combination being less than 1000 Da.

A further polyalkylene glycol may be polyethylene glycol (PEG) and/or polypropylene glycol (PPG). The PEG and/or PPG may comprise any desired molecular weight. The desired molecular weight is the average molecular weight in the range of from 200 Da to 8000 Da.

The polyurethane-based resin may further comprise a polyetheramine. Suitable polyetheramines include but are not limited to amine-terminated polyethers having repeating units of ethylene oxide, propylene oxide, tetramethylene oxide or combinations thereof and having an average molecular weight in the range of about 230 to 4000 Da. Preferred polyetheramines have propylene oxide repeating units. Jeffamine® D4000 is a specific polyetheramine, a polyoxypropylene diamine, having an average molecular weight of about 4000 Da.

The ionically-charged modifier herein comprises a combination of anionic and cationic modifiers or a zwitterionic modifier that make the polyurethane zwitterionic in nature to render the resulting medical article with desirable properties. Resulting medical articles may advantageously have desirable surface properties including but not limited to antimicrobial and/or anti-fouling properties.

Including an ionically-charged modifier such as a combination of anionic and cationic modifiers or a zwitterionic modifier in the polyurethane resin such that a separate surface coating process to introduce antimicrobial/antithrombogenic agents may not be needed, can offer the following advantages: (i) simple zwitterionic TPU copolymer composition with passive non-fouling surface, without leach-out concern of the active agents; (ii) no capital investment for coating process; (iii) much reduced manufacturing/conversion costs; (iv) less environment, health and safety (EHS) impact; (v) less regulatory concern, e.g., heparin-induced thrombocytopenia (HIT).

Antimicrobial agents that can be used for bonding with anionic functional moieties of the zwitterionic polyurethane include any cationic antibiotics. Non-limiting examples of the cationic antibiotics include chlorhexidine acetate, chlorhexidine gluconate, silver sulfadiazine, benzalkonium chloride and cetylpyridinium chloride. In addition, cationic quaternary ammonium and guanidine containing biocides, cationic antimicrobial polymers, antimicrobial peptides or peptide-mimics as well as antifouling phospholipids or phospholipid-mimics can also be ionically bonded with anionic functional moieties of the zwitterionic polyurethane to actively and/or passively provide advantages of enhanced surface properties including antimicrobial and/or anti-fouling. Antimicrobial agents that can be used for bonding with cationic functional moieties of the zwitterionic polyurethane include any anionic antibiotics. Non-limiting examples of the anionic antibiotics include cloxacillin salt, cefoxitin salt, cefazolin salt, penicillin salt, or derivatives thereof. Non-limiting examples of the anionic antithrombogenic agents include heparin salt, or derivatives thereof. In addition, the skilled artisan will recognize that other cationic and/or anionic biocides and anticoagulants of either small molecules or macromolecules can also be used for bonding with ionic functional groups of the zwitterionic polyurethane.

Should an antimicrobial/antithrombogenic bonding nonetheless be desired to achieve desirable material surface antimicrobial/anti-fouling properties, the technology herein at least has the following advantages: (i) ionic bonding of antimicrobial/antithrombogenic agents onto zwitterionic TPU polymer substrates to achieve non-leaching or controlled release of active agents; (ii) polymer substrates already have ionic functionalities for bonding of active agents and no priming (e.g., chemical or plasma treatments) of polymer substrates is needed, which would simplify medical device manufacturing process and significantly reduce conversion costs; iii) ionic antimicrobial and/or anti-thrombogenic agents would be ionically bonded not only on zwitterionic TPU surface but also in the bulk zwitterionic TPU for potential continuous and long-term antimicrobial/antithrombogenic agent supply to device surface.

Furthermore, cationic radiopaque agent, including but not limited to barium and bismuth cations, can also be ionically bonded with anionic functional moieties of the zwitterionic polyurethane to provide medical article desirable radiopacity.

The ionically-charged modifier may be a combination of anionic and cationic modifiers or a zwitterionic modifier.

The anionic modifier may comprise one or more of —$SO_3^-$ and/or $COO^-$ functional moieties. Non-limiting examples of the anionic modifiers are: bis-1,4-((2-hydroxypropoxy)-2-propoxy)-butane sulfonate sodium salt (SULFADIOL®-7Q); 2,3-dihydroxypropane-1-sulfonate sodium salt; N,N-bis(2-hydroxyethyl)-2-aminoethanesulfonate sodium salt; 2,2-bis(hydroxymethyl)propionic acid; 2,2-bis(hydroxymethyl)butyric acid (BHMBA); or combination thereof.

The cationic modifier may comprise one or more quaternary ammonium functional moieties. A non-limiting example of the cationic modifier with quaternary ammonium functional moiety is bis(2-hydroxyethyl)dimethylammonium chloride (BHDAC).

The zwitterionic modifier may comprise both anionic and cationic functional moieties. Non-limiting examples of the zwitterionic modifier with both anionic and cationic functional moieties are: N,N-bis(2-hydroxyethyl)-2-amino-ethanesulfonic acid; N,N-bis(2-hydroxyethyl)glycine; or combination thereof.

In one or more embodiments, the medical articles herein are effective to reduce thrombus formation and/or bacterial biofilm.

The polyurethanes described herein may be fabricated into film, tubing, and other forms by conventional thermoplastic fabricating techniques including melt casting, compounding, extrusion/coextrusion, molding, etc. The polyurethane described herein may be used for PICCs, PIVCs, and CVCs. The polymer may have incorporated therein, as desired, conventional stabilizers, additives (e.g., a radiopaque filler), and/or processing aids. The amounts of these materials will vary depending upon the application of the polyurethane, but if present, are typically in amounts so in the range of from 0.1 to 50 weight percent of the final compound.

Polyurethanes Including Low-Surface Energy Modifying Oligomers

Optionally, the polyurethanes herein may further comprise low-surface energy modifying oligomers to provide further surface enhancements as described in commonly-assigned, co-pending U.S. Ser. No. 16/577,824 and Ser. No. 16/577,826, filed Sep. 20, 2019 (WO 2020/068617 A1 and WO 2020/068619 A1), incorporated herein by reference. An advantage of low-surface energy modified polyurethane materials is that their non-sticking, hydrophobic surfaces can provide antimicrobial, self-lubricating and/or anti-fouling properties.

The polyurethanes including low-surface energy modifying oligomers may be produced by the reaction of: a diisocyanate, a diol chain extender, at least one polyglycol, an ionically-charged modifier (a combination of anionic and cationic modifiers or a zwitterionic modifier), and a low-surface energy modifying oligomer. In an embodiment, modified polyurethanes comprise a hard segment content in the range of from 25% to 75% and a soft segment content in the range of from 75% to 25% by weight.

Polymerization of the polyurethane to include a low-surface energy modifying oligomer may be a one-step or a two-step copolymerization process. The process may require a catalyst, solvent, other additives, or a combination thereof. The synthesis can also be achieved by a variety of other synthesis techniques with or without catalyst/solvent understood by those skilled in the art.

The low-surface energy modifying oligomers contain functional moieties that migrate onto the polyurethane surface to render the resulting medical article desirable surface properties. Non-limiting examples of the low-surface energy modifying oligomer include fluoroether, silicone, or combination thereof. In one or more embodiments, the low-surface energy modifying oligomers have at least one, preferably two, alcohol moieties (C—OH).

A low-surface energy modifying oligomer for the backbone may comprise a diol-containing perfluoropolyether.

In one or more embodiments, the diol-containing perfluoropolyether has the following structure.

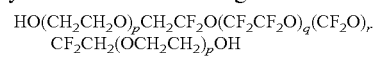

Wherein total of values for p+q+r are such that the fluorine content of the oligomer may be in the range of from 55% to 60% by weight and the average molecular weight of the oligomer is in the range of from 1500 to 2200 Da.

An exemplary diol-containing perfluoropolyether (PFPE) may be a commercial product sold under the trade name Fluorolink® E10-H, which is a dialcohol-terminated, ethoxylated PFPE, with about 1,700 Da average molecular weight and about 57% w/w fluorine content.

A low-surface energy modifying oligomer as a side chain may comprise a monofunctional polysiloxane. In one or more embodiments, the monofunctional polysiloxane is a monodialcohol-terminated polydimethylsiloxane (PDMS) having the following structure.

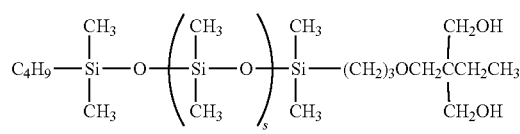

wherein, s may be in the range of from 5 to 200.

Exemplary monodialcohol-terminated polydimethylsiloxanes may be a commercial product sold under the product codes MCR-C61, MCR-C62 and MCR-C63. MCR-C62 has an average molecular weight of 5000 Da (s in range of 62-63), MCR-C61 has an average molecular weight of 1000 Da (s in range of 8-9), and MCR-C63 has an average molecular weight of 15,000 Da (s in range of 197-198). In one or more embodiments, the low-surface energy modifying oligomer for the as a side chain is MCR-C62.

Bonding of Active Agents with Polyurethane-Based Resins

In one or more embodiments, the polyurethane-based resin is bound to an ionic agent through ionic bonding. In various embodiments, the ionic agent comprises one or more of: an antimicrobial agent, a lubricating agent, a radiopaque agent, and an antithrombotic agent.

Antimicrobial agents that can be used for bonding with anionic functional moieties of the zwitterionic polyurethane include any cationic antibiotics. Non-limiting examples of the cationic antibiotics include chlorhexidine acetate, chlorhexidine gluconate, silver sulfadiazine, benzalkonium chloride and cetylpyridinium chloride. In addition, cationic quaternary ammonium and guanidine containing biocides, cationic antimicrobial polymers, antimicrobial peptides or peptide-mimics as well as antifouling phospholipids or phospholipid-mimics can also be ionically bonded with anionic functional moieties of the zwitterionic polyurethane to actively and/or passively provide advantages of enhanced surface properties including antimicrobial and/or anti-fouling. Antimicrobial agents that can be used for bonding with cationic functional moieties of the zwitterionic polyurethane include any anionic antibiotics. Non-limiting examples of the anionic antibiotics include cloxacillin salt, cefoxitin salt, cefazolin salt, penicillin salt, or derivatives thereof. Non-limiting examples of the anionic antithrombogenic agents include heparin salt, or derivatives thereof. In addition, the skilled artisan will recognize that other cationic and/or anionic biocides and anticoagulants of either small molecules or macromolecules can also be used for bonding with ionic functional groups of the zwitterionic polyurethane.

Furthermore, cationic radiopaque agent, including but not limited to barium and bismuth cations, can also be ionically bonded with anionic functional moieties of the zwitterionic polyurethane to provide medical article desirable radiopacity.

Ionic bonding of active agents can be achieved by solution imbibing technique or bulk mixing (e.g., thermal compounding or solvent mixing) technique. As a result, ionic antimicrobial, antithrombogenic, and/or radiopaque agents would be ionically bonded not only on zwitterionic TPU surface but also in the bulk zwitterionic TPU to render the resulting medical device desirable properties, including antimicrobial, anti-fouling, and/or radiopacity.

In one or more embodiments, the medical articles herein are effective to provide antimicrobial and/or anti-fouling activity. In one or more embodiments, the medical articles actively provide enhanced surface properties including antimicrobial and/or anti-fouling activity.

General Procedure for Polyurethane Synthesis

Method 1

The zwitterionic polyurethanes discussed herein may be prepared by a one-step or two-step copolymerization process using a zwitterionic modifier during copolymerization. The process may require a catalyst, solvent, other additives, or a combination thereof. The synthesis may also be achieved by a variety of other synthesis techniques with or without catalyst/solvent understood by those skilled in the art. The zwitterionic modifier may comprise both anionic and cationic functional moieties. Non-limiting examples of the zwitterionic modifier with both anionic and cationic functional moieties are: N,N-bis(2-hydroxyethyl)-2-amino-ethanesulfonic acid; N,N-bis(2-hydroxyethyl)glycine; or combination thereof. Table I shows exemplary formulations.

Table I. Exemplary Formulations of Polyurethane Resins with the proviso that the ingredients total 100%.

TABLE I

| Reactant | I-A by weight | I-B by weight | I-C by weight |
|---|---|---|---|
| Diisocyanate | 24-75% | 24-70% | 24-65% |
| Total Poly glycol | 15-75% | 20-70% | 25-65% |
| Regular Diol Chain Extender | 0.01-25% | 0.01-25% | 0.01-25% |
| Zwitterionic Modifier | 0.01-10% | 0.01-10% | 0.01-10% |
| Modifying Oligomer (Optional) | 0-10% | 0-10% | 0-10% |
| Hard Segment % | 25-75% | 30-70% | 35-65% |

Method 2

The zwitterionic polyurethanes discussed herein may be prepared by a one-step or two-step copolymerization process using a combination of anionic and cationic modifiers during copolymerization. A combination of anionic modifiers and cationic modifiers during copolymerization will provide resulting polyurethanes a zwitterionic nature. The anionic modifier may comprise one or more of —$SO_3^-$ and/or $COO^-$ functional moieties. Non-limiting examples of the anionic modifiers are: bis-1,4-((2-hydroxypropoxy)-2-propoxy)-butane sulfonate sodium salt (SULFADIOL®-7Q); 2,3-dihydroxypropane-1-sulfonate sodium salt; N,N-bis(2-hydroxyethyl)-2-aminoethanesulfonate sodium salt; 2,2-bis(hydroxymethyl)propionic acid; 2,2-bis(hydroxymethyl) butyric acid (BHMBA); or combination thereof. The cationic modifier may comprise one or more quaternary ammonium functional moieties. A non-limiting example of the cationic modifier with quaternary ammonium functional moiety is bis(2-hydroxyethyl)dimethylammonium chloride (BHDAC).

Method 3

The zwitterionic polyurethanes discussed herein may be formulated from a blend of two or more different polyurethane compositions, e.g., blending/compounding of existing anionic polyurethanes and cationic polyurethanes in various weight ratios ranging from 0.01-100. Blending/compounding approach can allow for quick creation and characterization of new polyurethane compositions using the already existing polyurethane copolymers. Even though the microdomain structure and molecular weight distribution may be different using direct copolymerization approach (METHOD 2) compared to blending/compounding approach (METHOD 3), it is expected that comparable material properties will result based on a comparable overall polyurethane composition.

Exemplary Polyurethane-Based Resins

Medical articles are formed from a polyurethane-based resin, which is a blend of an anionic polyurethane and a cationic polyurethane at a certain ratio. The hard segment content of the resulting zwitterionic polyurethane is in the range of from 25% to 75% by weight, and the soft segment content of the resin is in the range of from 75% to 25% by weight.

In one or more embodiments, the anionic polyurethane has the following ingredients: the diisocyanate comprises 4,4'-diphenylmethane diisocyanate (MDI); the diol chain extender comprises 1,4-butanediol; the polyglycols comprise a polytetramethylene ether glycol (PTMEG) with average MW in the range of from 250 Da to 2900 Da (n=3-40); the optional low-surface energy modifying oligomers comprise a diol-containing perfluoropolyether and/or a monofunctional polysiloxane; and the anionic modifier comprises 2,2-bis(hydroxymethyl) butyric acid (BHMBA) and/or bis-1,4-((2-hydroxypropoxy)-2-propoxy)-butane sulfonate sodium salt (SULFADIOL®-7Q). In one or more embodimets, the cationic polyurethane has the following ingredients: the diisocyanate comprises 4,4'-diphenylmethane diisocyanate (MDI); the diol chain extender comprises 1,4-butanediol; the polyglycols comprise a polytetramethylene ether glycol (PTMEG) with average MW in the range of from 250 Da to 2900 Da (n=3-40); the optional low-surface energy modifying oligomers comprise a diol-containing perfluoropolyether and/or a monofunctional polysiloxane; and the cationic modifier comprises bis(2-hydroxyethyl)dimethylammonium chloride (BHDAC).

Medical Articles of Polyurethane

Medical articles may be any plastic part of a fluid path. Exemplary medical articles that may be formed by the polyurethanes disclosed herein may be a component of a catheter; a needle/needleless connector; or tubing. Exemplary devices are: central venous catheters, peripherally-inserted central catheters, and peripheral intravenous catheters. Catheter tubing can be formed through compounding and extrusion/coextrusion processes. During compounding, granulates of synthesized polyurethanes or blend of two or more polyurethanes, and an optional radiopaque filler are added into a twin-screw compounder simultaneously. The mix ratio can be controlled and adjusted by a gravimetric multiple-feeder system. The mixed polyurethane melt (conveying through multiple heating zones) continuously passes through a die, a quench tank, and is subsequently cut into regular-sized pellets by a puller-pelletizer. The collected pellets are used to be fed into an extruder/coextruder to form a catheter tube, depending on tubing's specific configuration.

Medical articles formed from zwitterionic polyurethane resins disclosed herein can potentially possess inherent antimicrobial and/or anti-fouling surface properties.

Antimicrobial agents that can be used for bonding with anionic functional moieties of the zwitterionic polyurethane include any cationic antibiotics. Non-limiting examples of the cationic antibiotics include chlorhexidine acetate, chlorhexidine gluconate, silver sulfadiazine, benzalkonium chloride and cetylpyridinium chloride. In addition, cationic quaternary ammonium and guanidine containing biocides, cationic antimicrobial polymers, antimicrobial peptides or peptide-mimics as well as antifouling phospholipids or phospholipid-mimics can also be ionically bonded with anionic functional moieties of the zwitterionic polyurethane to actively and/or passively provide advantages of enhanced surface properties including antimicrobial and/or anti-fouling. Antimicrobial agents that can be used for bonding with cationic functional moieties of the zwitterionic polyurethane include any anionic antibiotics. Non-limiting examples of the anionic antibiotics include cloxacillin salt, cefoxitin salt, cefazolin salt, penicillin salt, or derivatives thereof. Non-limiting examples of the anionic antithrombogenic agents include heparin salt, or derivatives thereof. In addition, the skilled artisan will recognize that other cationic and/or anionic biocides and anticoagulants of either small molecules or macromolecules can also be used for bonding with ionic functional groups of the zwitterionic polyurethane.

Furthermore, cationic radiopaque agent, including but not limited to barium and bismuth cations, can also be ionically bonded with anionic functional moieties of the zwitterionic polyurethane to provide medical article desirable radiopacity.

Ionic bonding of active agents can be achieved by solution imbibing technique or bulk mixing (e.g., thermal compounding or solvent mixing) technique. As a result, ionic antimicrobial, antithrombogenic, and/or radiopaque agents would be ionically bonded not only on zwitterionic TPU surface but also in the bulk zwitterionic TPU to render the resulting medical device desirable properties, including antimicrobial, anti-fouling, and/or radiopacity.

EXAMPLES

Example 1

Anionic thermoplastic polyurethane (TPU) resins were made in accordance with Table 2 by the one-step copolymerization process (no catalyst or solvent) using a pilot-scale polyurethane (PU) processor. Exemplary formulations had MDI as an aromatic diisocyanate, a combination of polytetramethylene ether glycols (PTMEGs with average molecular weight of 500-1000 Da), 1,4-butanediol as the chain extender, and 2,2-bis(hydroxymethyl)butyric acid (BHMBA) as the anionic modifier according to Table 2. No low-surface energy modifying oligomer was present. Reference polyurethane without an ionic modifier (Reference PU-A) was made as well. Table 2 shows the anionic TPU copolymer compositions.

TABLE 2

| Example | Total Hard Segment Content | Anionic Modifier | Location of Anionic Modifier | Anionic Modifier Content |
|---|---|---|---|---|
| CP-1 | 61.0 wt. % | BHMBA | Chain Extender Hard Segment | 0.96 wt. % |
| CP-2 | 61.0 wt. % | BHMBA | Chain Extender Hard Segment | 2.48 wt. % |

Cationic thermoplastic polyurethane (TPU) resins were made in accordance with Table 3 by the one-step copolymerization process (no catalyst or solvent) using a pilot-scale polyurethane (PU) processor. Exemplary formulations had MDI as an aromatic diisocyanate, a combination of polytetramethylene ether glycols (PTMEGs with average molecular weight of 500-1000 Da), 1,4-butanediol as the chain extender, and bis(2-hydroxyethyl)dimethylammonium chloride (BHDAC) as the cationic modifier according to Table 3. No low-surface energy modifying oligomer was present. Table 3 shows the cationic TPU copolymer compositions.

TABLE 3

| Example | Total Hard Segment Content | Cationic Modifier | Location of Cationic Modifier | Cationic Modifier Content |
|---|---|---|---|---|
| Q-PU-2 | 61.0 wt. % | BHDAC | Chain Extender Hard Segment | 0.96 wt. % |
| Q-PU-3 | 61.0 wt. % | BHDAC | Chain Extender Hard Segment | 2.51 wt. % |

The anionic TPU granulates/chips (e.g., CP-1 and CP-2) and cationic TPU granulates/chips (e.g., Q-PU-2 and Q-PU-3) were blended and extruded into zwitterionic TPU ribbon sheets (METHOD 3) for material property characterization. The thickness of the ribbon sheets was 0.007-0.010 in. Table 4 shows both the benchmark reference (Reference PU-A) and the zwitterionic TPU copolymer compositions.

TABLE 4

| Example | Total Hard Segment Content | Anionic Modifier | Anionic Modifier Content | Cationic Modifier | Cationic Modifier Content |
|---|---|---|---|---|---|
| Z-PU-1 | 61.0 wt. % | BHMBA | 0.48 wt. % | BHDAC | 0.48 wt. % |
| Z-PU-2 | 61.0 wt. % | BHMBA | 1.24 wt. % | BHDAC | 1.26 wt. % |
| Reference PU-A | 61.0 wt. % | NONE | NONE | NONE | NONE |

New zwitterionic TPU Z-PU-1 was prepared by 50/50 wt. % blend of anionic TPU CP-1 and cationic TPU Q-PU-2; new zwitterionic TPU Z-PU-2 was prepared by 50/50 wt. % blend of anionic TPU CP-2 and cationic PTU Q-PU-3.

Example 2

Testing

Calculation of Ion Exchange Capacity. The ion exchange capacity (mmol/gm) of zwitterionic TPUs can be easily calculated based on the material compositions as shown in Table 5.

TABLE 5

| Example | Anionic Modifier Content | Cation Exchange Capacity (mmol/gm) | Cationic Modifier Content | Anion Exchange Capacity (mmol/gm) |
|---|---|---|---|---|
| Z-PU-1 | 0.48 wt. % | 0.032 | 0.48 wt. % | 0.028 |
| Z-PU-2 | 1.24 wt. % | 0.084 | 1.26 wt. % | 0.074 |
| Reference PU-A | NONE | 0 | NONE | 0 |

Tensile Property Testing. Tensile properties of both the reference and the zwitterionic PU ribbons (thickness of 0.007-0.010 in.) were characterized using Instron. The testing was performed at room conditions (23° C., 50% RH, and >40 h equilibration time), which is provided in Table 6 (mean of 10 measurements for each data).

TABLE 6

| EXAMPLE | Tensile at break (psi) Elongation at break (%) | Tensile at 5% strain (psi) | Tensile at 25% strain (psi) | Tensile at 50% strain (psi) | Tensile at 100% strain (psi) | Tensile at 200% strain (psi) | Young's Modulus (MPa) |
|---|---|---|---|---|---|---|---|
| Z-PU-1 | 11245.06 335.02 | 2151.95 | 2304.20 | 2594.65 | 3567.61 | 6208.78 | 504.62 |
| Z-PU-2 | 9114.47 338.51 | 1611.69 | 1891.09 | 2153.55 | 2947.76 | 5105.00 | 369.31 |
| Reference PU-A | 11003.46 306.27 | 2317.78 | 2537.44 | 2904.74 | 3932.39 | 6707.76 | 528.77 |

Testing was also performed at body indwell conditions (37° C., water equilibration for 4 hours), which is provided in Table 7 (mean of 10 measurements for each data). Soften ratio is defined according to the following Equation (1).

$$\text{Soften Ratio} = \frac{\text{Young's Modulus at Room Conditions} - \text{Young's Modulus at Body Indwell Conditions}}{\text{Young's Modulus at Room Conditions}} \times 100\% \qquad \text{Equation (1)}$$

TABLE 7

| EXAMPLE | Tensile at break (psi) Elongation at break (%) | Tensile at 5% strain (psi) | Tensile at 25% strain (psi) | Tensile at 50% strain (psi) | Tensile at 100% strain (psi) | Tensile at 200% strain (psi) | Young's Modulus (MPa) | Soften Ratio (%) |
|---|---|---|---|---|---|---|---|---|
| Z-PU-1 | 10118.01 398.90 | 381.09 | 903.90 | 1149.22 | 1576.16 | 3338.94 | 63.73 | 87.37 |
| Z-PU-2 | 7147.22 409.41 | 302.47 | 734.81 | 931.09 | 1214.59 | 2348.18 | 49.67 | 86.55 |
| Reference PU-A | 9500.22 343.55 | 408.47 | 992.86 | 1268.98 | 1820.49 | 3970.41 | 62.66 | 88.15 |

Tables 6 and 7 show that the new zwitterionic TPUs exhibited desirable tensile properties and material soften ratios for medical device applications.

Embodiments

Various embodiments are listed below. It will be understood that the embodiments listed below may be combined with all aspects and other embodiments in accordance with the scope of the invention.

Embodiment (a). A medical article formed from a polyurethane-based resin, which is a reaction product of ingredients comprising: a diisocyanate; a diol chain extender; a polyglycol; and a zwitterionic modifier or a combination of anionic and cationic modifiers incorporated into a backbone, as a side chain, or both of the polyurethane-based resin formed by the diisocyanate, the polyglycol, and the diol chain extender; the polyurethane-based resin having a hard segment content in a range of from 25% to 75% by weight and a soft segment content of the resin is in a range of from 75% to 25% by weight.

Embodiment (b). The medical article of embodiment (a), which is effective to reduce thrombus formation and/or bacterial biofilm formation.

Embodiment (c). The medical article of embodiment (a) to embodiment (b), wherein the anionic modifier comprises an anionic functional moiety of $-SO_3^-$, $-COO^-$, or combination thereof.

Embodiment (d). The medical article of embodiment (a) to embodiment (c), wherein the anionic modifier comprises one or more of: bis-1,4-((2-hydroxypropoxy)-2-propoxy)-butane sulfonate sodium salt (SULFADIOL®-7Q); 2,3-dihydroxypropane-1-sulfonate sodium salt; N,N-bis(2-hydroxyethyl)-2-aminoethanesulfonate sodium salt; 2,2-bis(hydroxymethyl)propionic acid; 2,2-bis(hydroxymethyl)butyric acid (BHMBA); or combination thereof.

Embodiment (e). The medical article of embodiment (a) to embodiment (d), wherein the cationic modifier comprises a cationic functional moiety of quaternary ammonium.

Embodiment (f). The medical article of embodiment (a) to embodiment (e), wherein the cationic modifier comprises: bis(2-hydroxyethyl)dimethylammonium chloride (BHDAC).

Embodiment (g). The medical article of embodiment (a) to embodiment (f), wherein the zwitterionic modifier comprises at least one anionic functional moiety and at least one cationic functional moiety, the anionic functional moiety comprises $-SO_3^-$, $-COO^-$ or combination thereof and the cationic functional moiety comprises quaternary ammonium.

Embodiment (h). The medical article of embodiment (a) to embodiment (g), wherein the zwitterionic modifier comprises: N,N-bis(2-hydroxyethyl)-2-amino-ethanesulfonic acid; N,N-bis(2-hydroxyethyl)glycine; or combination thereof.

Embodiment (i). The medical article of embodiment (a) to embodiment (h), wherein the ingredients of the reaction product consist essentially of: 4,4'-diphenylmethane diisocyanate (MDI) as the diisocyanate; 1,4-butanediol as the diol chain extender; a polytetramethylene ether glycol as the polyglycol; bis(2-hydroxyethyl)dimethylammonium chloride (BHDAC) as the cationic modifier; and 2,2-bis(hydroxymethyl)butyric acid (BHMBA) and/or bis-1,4-((2-hydroxypropoxy)-2-propoxy)-butane sulfonate sodium salt (SULFADIOL®-7Q) as the anionic modifier.

Embodiment (j). The medical article of embodiment (a) to embodiment (i), wherein the ionic modifier is present in an amount of greater than or equal to 0.01 weight percent of the overall composition of the polyurethane-based resin.

Embodiment (k). The medical article of embodiment (a) to embodiment (j), wherein the ionic modifier is present in an amount of less than or equal to 75 weight percent of the overall composition of the polyurethane-based resin.

Embodiment (l). The medical article of embodiment (a) to embodiment (k), wherein the diisocyanate is selected from the group consisting of: an aliphatic diisocyanate, alicyclic diisocyanate and an aromatic diisocyanate.

Embodiment (m). The medical article of embodiment (a) to embodiment (l), wherein the diisocyanate is selected from the group consisting of: 4,4'-diphenylmethane diisocyanate (MDI), toluene diisocyanate (TDI), isophorone diisocyanate (IPDI), methylene-bis(4-cyclohexylisocyanate) (HMDI), and combinations thereof.

Embodiment (n). The medical article of embodiment (a) to embodiment (m), wherein the diol chain extender is selected from the group consisting of: ethylene glycol, 1,3-propylene glycol, 1,4-butanediol, neopentyl glycol, and alicyclic glycols having up to 10 carbon atoms.

Embodiment (o). The medical article of embodiment (a) to embodiment (n), wherein the polyglycol is selected from the group consisting of: polyalkylene glycol, polyester glycol, polycarbonate glycol, and combinations thereof.

Embodiment (p). The medical article of embodiment (a) to embodiment (o), wherein the polyglycol comprises the polyalkylene glycol.

Embodiment (q). The medical article of embodiment (a) to embodiment (p), wherein the polyalkylene glycol comprises a polytetramethylene ether glycol.

Embodiment (r). The medical article of embodiment (a) to embodiment (q), wherein the polyurethane-based resin is bound to an ionic agent through ionic bonding, which is effective to actively provide enhanced surface properties including antimicrobial and/or anti-fouling activity.

Embodiment (s). A method of infusion therapy comprising: infusing a material from a medical article according to any of embodiment (a) to embodiment (r) into a patient.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A medical article formed from a polyurethane-based resin, which is a reaction product of ingredients comprising:
   a diisocyanate;
   a diol chain extender;
   a polyglycol; and
   a zwitterionic modifier or a combination of anionic and cationic modifiers incorporated into a backbone, as a side chain, or both of the polyurethane-based resin formed by the diisocyanate, the polyglycol, and the diol chain extender, wherein the zwitterionic modifier comprises at least one anionic functional moiety and at least one cationic functional moiety, the anionic functional moiety comprises —$SO_3^-$, or a combination of —$COO^-$ and —$SO_3^-$, and the cationic functional moiety comprises quaternary ammonium, and wherein the anionic modifier comprises —$SO_3^-$, or a combination of —$COO$ and —$SO_3^-$, and the cationic modifier comprises quaternary ammonium;
   the polyurethane-based resin having a hard segment content in a range of from greater than 60% to 75% by weight and a soft segment content of the resin is in a range of from 25% 25% to less than 40% by weight.

2. The medical article of claim 1, which is effective to reduce thrombus formation and/or bacterial biofilm formation.

3. The medical article of claim 1, wherein the anionic modifier comprises one or more of: bis-1,4-((2-hydroxypropoxy)-2-propoxy)-butane sulfonate sodium salt; 2,3-dihydroxypropane-1-sulfonate sodium salt; N,N-bis(2-hydroxyethyl)-2-aminoethanesulfonate sodium salt; 2,2-bis(hydroxymethyl) propionic acid; 2,2-bis(hydroxymethyl) butyric acid (BHMBA); or combination thereof.

4. The medical article of claim 1, wherein the cationic modifier comprises: bis(2-hydroxyethyl)dimethylammonium chloride (BHDAC).

5. The medical article of claim 1, wherein the zwitterionic modifier comprises: N,N-bis(2-hydroxyethyl)-2-amino-ethanesulfonic acid, or a combination of N,N-bis(2-hydroxyethyl)-2-amino-ethanesulfonic acid and N, N-bis(2-hydroxyethyl)glycine.

6. The medical article of claim 1, wherein the ingredients of the reaction product consist essentially of:
   4,4'-diphenylmethane diisocyanate (MDI) as the diisocyanate;
   1,4-butanediol as the diol chain extender;
   a polytetramethylene ether glycol as the polyglycol;
   bis(2-hydroxyethyl)dimethylammonium chloride (BHDAC) as the cationic modifier; and
   bis-1,4-((2-hydroxypropoxy)-2-propoxy)-butane sulfonate sodium salt, or 2,2-bis(hydroxymethyl) butyric acid (BHMBA) and bis-1,4-((2-hydroxypropoxy)-2-propoxy)-butane sulfonate sodium salt as the anionic modifier.

7. The medical article of claim 1, wherein the zwitterionic, cationic, or anionic modifier is present in an amount of greater than or equal to 0.01 weight percent of the overall composition of the polyurethane-based resin.

8. The medical article of claim 1, wherein the zwitterionic, cationic, or anionic modifier is present in an amount of less than or equal to 75 weight percent of the overall composition of the polyurethane-based resin.

9. The medical article of claim 1, wherein the diisocyanate is selected from the group consisting of: an aliphatic diisocyanate, alicyclic diisocyanate and an aromatic diisocyanate.

10. The medical article of claim 1, wherein the diisocyanate is selected from the group consisting of: 4,4'-diphenylmethane diisocyanate (MDI), toluene diisocyanate (TDI), isophorone diisocyanate (IPDI), methylene-bis(4-cyclohexylisocyanate) (HMDI), and combinations thereof.

11. The medical article of claim 1, wherein the diol chain extender is selected from the group consisting of: ethylene glycol, 1,3-propylene glycol, 1,4-butanediol, neopentyl glycol, and alicyclic glycols having up to 10 carbon atoms.

12. The medical article of claim 1, wherein the polyglycol is selected from the group consisting of: polyalkylene glycol, polyester glycol, polycarbonate glycol, and combinations thereof.

13. The medical article of claim 1, wherein the polyglycol comprises the polyalkylene glycol.

14. The medical article of claim 13, wherein the polyalkylene glycol comprises a polytetramethylene ether glycol.

15. The medical article of claim 1, wherein the polyurethane-based resin is bound to an ionic agent through ionic bonding, which is effective to actively provide enhanced surface properties including antimicrobial and/or anti-fouling activity.

16. A method of infusion therapy comprising: infusing a material from a medical article according to claim 1 into a patient.

17. A medical article formed from a polyurethane-based resin, which is a reaction product of ingredients comprising:
   a diisocyanate comprising 4,4'-diphenylmethane diisocyanate (MDI);
   a diol chain extender comprising 1,4-butanediol;
   a polyglycol comprising polytetramethylene ether glycol; and
   a zwitterionic modifier or a combination of anionic and cationic modifiers incorporated into a backbone, as a side chain, or both of the polyurethane-based resin formed by the diisocyanate, the polyglycol, and the diol chain extender, the cationic modifier comprising bis(2-hydroxyethyl)dimethylammonium chloride (BHDAC), the anionic modifier comprising bis-1,4-((2-hydroxypropoxy)-2-propoxy)-butane sulfonate sodium salt, or 2,2-bis(hydroxymethyl) butyric acid (BHMBA) and bis-1,4-((2-hydroxypropoxy)-2-propoxy)-butane sulfonate sodium salt;
   the polyurethane-based resin having a hard segment content in a range of from 25% to 75% by weight and a soft segment content of the resin is in a range of from 75% to 25% by weight.

18. A medical article formed from a polyurethane-based resin, which is a reaction product of ingredients comprising:
   a diisocyanate comprising 4,4'-diphenylmethane diisocyanate (MDI);
   a diol chain extender comprising 1,4-butanediol;
   a polyglycol comprising a polytetramethylene ether glycol; and
   a zwitterionic modifier or a combination of anionic and cationic modifiers incorporated into a backbone, as a side chain, or both of the polyurethane-based resin formed by the diisocyanate, the polyglycol, and the diol chain extender, the cationic modifier comprising bis(2-hydroxyethyl)dimethylammonium chloride (BHDAC), the anionic modifier comprising one or more of bis-1,4-((2-hydroxypropoxy)-2-propoxy)-butane sulfonate sodium salt, 2,3-dihydroxypropane-1-sulfonate sodium salt, N,N-bis(2-hydroxyethyl)-2-aminoethanesulfonate sodium salt, 2,2-bis(hydroxymethyl) propionic acid, or 2,2-bis(hydroxymethyl) butyric acid (BHMBA), and the zwitterionic modifier comprising N, N-bis(2-hydroxyethyl)-2-amino-ethanesulfonic acid, or a combination of N,N-bis(2-hydroxyethyl)-2-amino-ethanesulfonic acid and N,N-bis(2-hydroxyethyl)glycine;
the polyurethane-based resin having a hard segment content in a range of from 25% to 75% by weight and a soft segment content of the resin is in a range of from 75% to 25% by weight.

\* \* \* \* \*